United States Patent [19]

Schreiber

[11] Patent Number: 4,607,091
[45] Date of Patent: Aug. 19, 1986

[54] POLYMERIC RESINS DERIVED FROM 1-OXA-3-AZA TETRALINE GROUP-CONTAINING COMPOUNDS AND CYCLOALIPHATIC EPOXIDES

[75] Inventor: Herbert Schreiber, Wollerau, Switzerland

[73] Assignee: Gurit-Essex AG, Freienbach, Switzerland

[21] Appl. No.: 774,433

[22] Filed: Sep. 10, 1985

[30] Foreign Application Priority Data

Sep. 14, 1984 [DE] Fed. Rep. of Germany ....... 3433851

[51] Int. Cl.$^4$ ...................... C08G 59/24; C08G 59/50
[52] U.S. Cl. ........................................ 528/96; 528/97; 525/504
[58] Field of Search ..................... 528/96, 97; 525/504

[56] References Cited

U.S. PATENT DOCUMENTS 3,749,683 7/1973 Tomalia et al. ..................... 528/96
4,383,102 5/1983 McDaniel et al. ............... 528/96 X Primary Examiner—Earl Nielsen
Attorney, Agent, or Firm—Yount & Tarolli

[57] ABSTRACT

A composition comprising a polymeric resin derived from (A) at least one compound containing an average of more than one 1-oxa-3-aza-tetraline group per molecule with (B) at least one cycloaliphatic epoxide containing at least two epoxide groups, at least one of said epoxide groups being part of said ring, the mole ratio of (B) to (A) being in the range of about 0.2 to about 2.

18 Claims, No Drawings

POLYMERIC RESINS DERIVED FROM 1-OXA-3-AZA TETRALINE GROUP-CONTAINING COMPOUNDS AND CYCLOALIPHATIC EPOXIDES

TECHNICAL FIELD

This invention relates to polymeric resins derived from 1-oxa-3-aza tetraline group-containing compounds and cycloaliphatic epoxides. More particularly, this invention relates polymeric resins derived from compounds containing an average of more than one 1-oxa-3-aza tetraline group, and cycloaliphatic epoxides containing at least one aliphatic ring and an average of at least two epoxide groups, at least one of said epoxide groups being part of said ring.

BACKGROUND OF THE INVENTION

Compounds containing 1-oxa-3-aza-tetraline groups, and their prepolymers, are known, for example, from Swiss Pat. Nos. 574,978, 579,113 and 606,169. They can be obtained, for example, from phenols by reaction with formaldehyde and an amine, according to the formula:

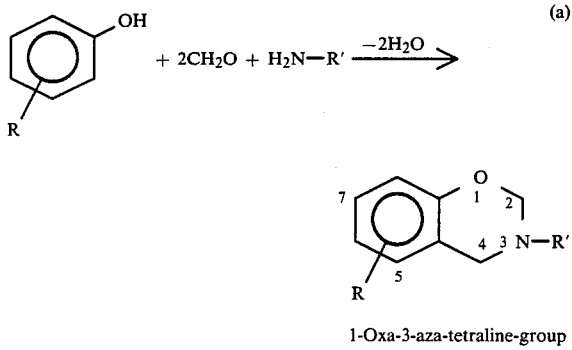

1-Oxa-3-aza-tetraline-group wherein R is, for example, hydrogen, halogen, alkyl or alkoxy, and R' is an aliphatic or aromatic group. In contrary to other known condensation reactions of phenols, amines and formaldehyde, in the reaction outlined above phenolic OH-groups are consumed. It is thereby possible, according to the formula (a) hereinabove, to determine the amount of the synthezised 1-oxa-3-aza tetraline group from the analytic determination of the said OH-groups in the reaction mixture.

It is also known from the above-mentioned patents that these compounds containing 1-oxa-3-aza-tetraline groups can be cured with epoxide resins, including cycloaliphatic epoxide resins. The products obtained up to now have been useful for various applications, but their stability is limited. The Martens heat stability of the hardest resins obtained up to now is only between about 120° C. and 135° C., with peak values from about 160° C. to 170° C.

For many applications, higher heat stabilities are necessary. For example, electric insulating materials of high heat stability are a constant requirement of the electric industry. Plastics reinforced with glass, quartz, carbon fibers and the like would probably be considered for many new areas of application if the heat resistance of the polymeric resin could be increased.

SUMMARY OF THE INVENTION

The present invention contemplates the provision of polymeric resins characterized by particularly outstanding heat stabilities in combination with good mechanical properties. Broadly stated, the present invention provides for a composition comprising a polymeric resin derived from (A) at least one compound containing an average of more than one 1-oxa-3-aza tetraline group per molecule with (B) at least one cycloaliphatic epoxide containing at least one aliphatic ring and an average of at least two epoxide groups, at least one of said epoxide groups being part of said ring, the mole ratio of (B) to (A) being in the range of about 0.2 to about 2.

DESCRIPTION OF THE PREFERRED EMBODIMENT

The polymeric resins provided in accordance with the present invention are derived from (A) compounds containing an average of more than one 1-oxa-3-aza-tetraline group per molecule and/or per pre-polymer of said compound and (B) cycloaliphatic epoxides containing at least one aliphatic ring and an average of at least two epoxide groups per molecule, at least one of said epoxide groups being part of said aliphatic ring and the remaining epoxide groups either being part of said ring or being directly attached to said ring.

Throughout this specification and in the appended claims, the terminology "part of a ring" with respect to the position of an epoxide group on an aliphatic ring refers to the following structure

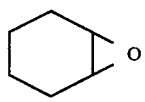

The terminology "directly attached to a ring" refers to the following structure

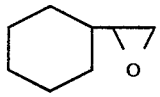

Compounds with more than one 1-oxa-3-aza-tetraline group in the molecule can be obtained from polyvalent phenols and/or amines, according to one of the following reaction schemes (b) or (c), or can be obtained by other methods known in the art.

In contrary to other known condensation reactions of phenols, amines and formaldehyde, in the reaction outlined above phenolic OH-groups are consumed. It is thereby possible, according to the formula (a) hereinabove, to determine the amount of the synthezised 1-oxa-3-aza tetraline groups from the analytic determination of the said OH-groups in the reaction mixture.

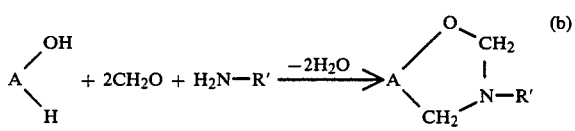

wherein:

is the nth part of a phenol with n phenol OH groups;

A is the group resulting from

after splitting off of OH and H in ortho position;

R' is an aliphatic or, preferably, an aromatic group; and n is a number greater than 1, preferably less than 6, more preferably from about 1.5 to about 3.

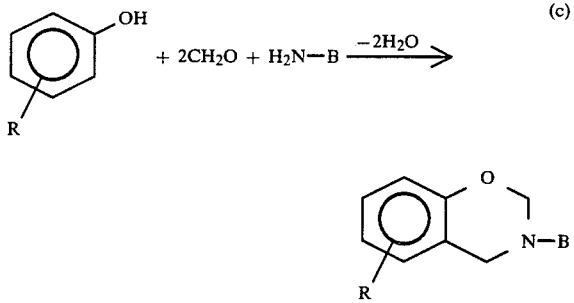

(c)

wherein:

B is the mth part of an m-valent aliphatic or, preferably, aromatic group, which may also contain hetero atoms, especially oxygen, or may be substituted by R;

R is hydrogen, halogen, alkyl or alkoxy with 1 to about 6 carbon atoms, preferably in meta- or para-position of the phenol; and m is a number greater than 1, preferably less than about 6, more preferably from about 1.5 to about 3.

The phenol nuclei may also be part of a condensed ring system.

Values of n or m that are not whole numbers mean that mixtures of different functional phenols or amines with the average value n or m are provided.

Suitable for use as 1-oxa-3-aza-tetraline group containing compounds are the reaction products which are prepared, for example, in accordance with the teachings of Swiss Pat. No. 606,169 (which is incorporated herein by reference), from phenols, amines and formaldehyde in non-stoichiometric proportions. Mole ratios of the reactants that provide an average of more than one 1-oxa-3-aza tetraline group per molecule must be used.

Prepolymers of 1-oxa-3-aza-tetraline group containing compounds are also useful in accordance with the invention. Since some of the 1-oxa-3-aza-tetraline groups may react during polymerization, these prepolymers may contain a fewer number of said 1-oxa-3-aza-tetraline groups than provided by the monomers used to form such prepolymers. It is essential, however, that the resulting prepolymers contain more than one 1-oxa-3-aza-tetraline group per molecule. This can be calculated by a skilled artisan from the functionality and the ratios of starting materials.

A 1-oxa-3-aza-tetraline composition according to the invention or the prepolymers thereof are obtained, for example, if per mole of multifunctional phenol or amine more than two moles of formaldehyde and more than one mole of monofunctional amine and phenol, respectively, are brought into reaction, whereby the mole proportions are within the limit defined by the disclosure of Swiss Pat. No. 606,169.

The reactants for forming the 1oxa-3-aza-tetraline group containing compounds of the invention are phenols or phenol derivatives, amines and formaldehyde. Examples of phenols that can be used include monovalent phenols, such as phenol and m- and p-cresol, m- and p-ethyl-phenol, m- and p-isopropylphenol, m- and p-methoxy-phenol, m- and p-ethoxy-phenol, m-and p-isopropyloxy-phenol, m- and p-chloro-phenol and B-naphthol. Meta-substituted phenols are preferred, since they do not include any blocked reactive positions. Ortho-substituted phenols are less appropriate. Bivalent phenols that are useful include 4,4'-dihydroxy-diphenylmethane, 3,3'-dihydroxydiphenylmethane, 2,2-bis-(4-hydroxyphenyl)-propane, 4,4'-dihydroxy-stilbene, hydroquinone, pyrocatechin and resorcin. Novolak resins mixed with a phenol can also be used.

Examples of amines that are useful include aniline, o-, m- and p-phenylene diamine, benzidine, 4,4'-diaminodiphenyl methane and 2,2-bis-(aminophenyl)-propane.

The epoxides are preferably bivalent or polyvalent cycloaliphatic epoxides containing at least one epoxide group in a ring, and the remaining epoxide groups also in a ring or directly attached to a ring. Preferred epoxides are epoxide resins represented by the formula

X—Y wherein:

X is a 3,4-epoxycyclohexyl group or a mono- or dimethyl substituted 3,4-epoxycyclohexyl group; and Y is a group of the formula

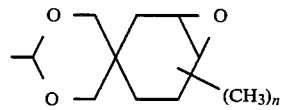

wherein n is a number in the range of from zero to 2, or a group of the formula

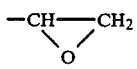

or a group of the formulae

—COO—CH$_2$—X or

—CH$_2$—Z—CH$_2$—X wherein:

X is as defined above, and Z is derived from an aliphatic, cycloaliphatic or aromatic dicarboxylic acid, such as, for example, adipic acid, terephthalic acid or 4,5-epoxy-hexahydrophthalic acid.

Particularly preferred epoxides are epoxide resins having equivalent weights in the range of from about 70 to about 250, preferably from about 120 to about 200.

Examples of epoxides that can be used include 2-(3,4-epoxy)cyclohexyl-5,5-spiro(3,4-epoxy)cyclohexane-m-dioxane, 1 to 4 times methylated 2-(3,4-epoxy)cyclohexyl-5,5-spiro(3,4-epoxy) cyclohexane-m-dioxane, 4-(1,2-epoxyethyl)-1,2-epoxycyclohexane, 1,2,8,9-diepoxy-p-methane, 2,2-bis(3,4-epoxycyclohexyl)propane, bis-(2,3-epoxycyclopentyl) ether, 1,2,5,6-diepoxy-4,7-hexahydromethanoindane, bis-(3,4-epoxy-cyclohexylmethyl) adipate, bis(3,4-epoxy-6-methylcyclohexylmethyl) adipate, bis-(3,4-epoxy-cyclohexylmethyl)terephthalate, bis-(3,4-epoxy-6-methyl-cyclohexylmethyl)-terephthalate,3,4-epoxy-cyclohexane carboxylic acid-(3,4-epoxy-cyclohexylmethyl) ester, 3,4-epoxy-6-methylcyclohexanecarboxylic acid-(3,4-epoxy-6-methylcyclohexylmethyl) ester, 1,2-bis-(5(1,2-epoxy)-4,7-hexahydromethanoindane oxy)-ethane 1,1,1-tris((5-(1,2-epoxy)-4,7-hexahydromethynoindane oxy)-methyl)-propane and 4,5-epoxyhexahydrophthalic acid-bis-(3,4-epoxy-cyclohexylmethyl) ester. Particularly preferred epoxide resins include 2-(3,4-epoxy)cyclohexyl-5,5-spiro(3,4-epoxy) cyclohexane-m-dioxane, 1 to 4 times methylated 2-(3,4-epoxy) cyclohexyl-5,5-spiro (3,4-epoxy)cyclohexane-m-dioxane, bis(3,4-epoxy-cyclohexylmethyl)adipate, bis(3,4-epoxy-6-methylcyclohexylmethyl)adipate, 3,4-epoxy-cyclohexane-carboxylic acid-(3,4-epoxy-cyclohexylmethyl) ester and 3,4-epoxy-6-methylcyclohexane carboxylic acid-(3,4-epoxy-6-methylcyclohexylmethyl) ester.

The mole ratio of epoxides to 1-oxa-3-aza-tetraline group containing compounds that are useful in accordance with the invention are preferably in the range of from about 0.2 to about 2, more preferably from about 0.8 to about 1.5.

For purposes of calculating equivalent ratios, the number of equivalents of a 1-oxa-3-aza-tetraline group containing compound is based on the amount of primary amine brought into reaction; independently of whether it actually forms part of a 1-oxa-3-aza-tetraline group. It is assumed that for each mole of formaldehyde that is reacted, one mole of water will be split off. Thus, for example, in Example 6 below, the theoretical equivalent weight of the 1oxa-3-aza-tetraline group containing compound is based on the following calculation

| 1 gram equivalent | Novolak (equiv. weight = 100) = | 100 g |
| +0.8 mole | analine = | 74.4 g |
| +1.5 mole | formaldehyde = | 45 g |
| −1.5 mole | water = | −27 g |
| | = | 192.4 g |

The N-equivalent weight is equal to 192.4 divided by 0.8 which equals 240.5.

If, in the production of the 1-oxa-3-aza-tetraline group containing compounds, no other nitrogen compounds other than the primary amines are added, the equivalent weight may also be calculated from the nitrogen content using known techniques. Compounds with more than one 1-oxa-3-aza-tetraline group per molecule have N-equivalent weights that are less than the average molecular weight.

The reaction between the 1-oxa-3-aza-tetraline group containing compound and epoxide, which is in effect a curing reaction, is preferably conducted at a temperature in the range of about 50° C. to about 300° C., more preferably about 100° C. to about 250° C., more preferably about 140° C. to about 230° C.

For various applications, it is advantageous to initially carry out the curing in at least two steps to produce as an intermediate product a solid or highly viscous, but still soluble or meltable, prepolymer. Alternatively, the prepolymer can be formed during the production of the 1-oxa-3-aza-tetraline group containing compound prior to reaction with the epoxide. The final curing step is then preferably carried out at a temperature in the range of about 140° C. to about 230° C.

The final curing step can be improved by addition of a catalyst to accelerate the reaction. In particular, the curing time can be shortened in this way. Examples of catalysts that can be used include, for example, acids, Friedel-Crafts catalysts, amines, phosphines or quaternizing agents for tertiary amines, and especially alkyl, aralkyl and aryl halides or sulfates, such as, for example, benzyl chloride, chlorobenzol, iodobenzol, iodoform, bromoform, methyl iodide or methyl sulfate.

Prior to or during the curing reaction to produce the polymeric resins of the invention, additives such as fillers, colorants, reinforcing fibers, plasticizers and the like can be added to the reaction mixture. These additives can be provied at levels of up to, for example, about 50% by weight of reaction mixture, preferably from about 10% to about 20% by weight of the mixture. The polymeric resins of the invention can also be combined with other plastics, resins or polymerizable monomers or prepolymers such as, for example, aldehyde condensation resins (e.g., phenol formaldehyde resins and other epoxide resins) prior to or during curing. The amount of the above mentioned additives which may be mixed with resin according to the invention or which are soluble therein should not exceed 50% of the mixture and preferably should be in the region of 10 to 20%.

The polymeric resins of the present invention can be used for many purposes such as, for example, casting, laminating, impregnating, coating, gluing, painting, binding or insulating, or in embedding, pressing, injection molding, extruding, sand mold binding, foam and ablative materials.

The polymeric resins of the invention are especially suitable for use in applications wherein relatively high heat stabilities are required. Thus, these resins are useful in electric coils, for example; their use permitting the use of higher voltages or the reduction of wire diameters. These resins are also useful in electric motors and in miniaturized electric devices and construction elements.

The polymeric resins of the invention are especially suitable for use in plastics reinforced with glass, quartz, carbon or aramide fibers, and the like. With the increase in heat stability resulting from the use of the polymeric resins of the invention, these reinforced plastics can be used for applications not previously suited for plastics such as, for example, in the replacement of metals or ceramic materials in heat-stressed construction applications. In these applications, the high bending resistance and impact strength of the resins of the invention are particularly advantageous.

In order to illustrate the preparation of the 1-oxa-3-aza-tetraline group containing compounds that are useful in the preparation of the polymeric resins of the invention, the following Examples 1-6 are provided. In the following examples as well as throughout the specification and claims, all parts and percentages are by weight and all temperatures are in degrees centigrade unless otherwise indicated.

EXAMPLE 1

210 grams of 30% formaldehyde (2.1 moles), 94 grams of phenol (1 mole) and 99 grams of 4,4′-diaminodiphenyl methane (0.5 mole) are added to a stirred vessel equipped with reflux cooling and heated to a temperature of 80° C. for 15 minutes. The mixture is allowed to settle. The top aqueous layer is separated, and the remaining water is distilled off in a vacuum at 100° C. The resulting resin-like 1-oxa-3-aza tetraline group containing compound has an N-equivalent weight of 217.

EXAMPLE 2

4.1 moles formaldehyde, 2 moles aniline, 1 mole of phenol and 0.5 mole bisphenol A (2,2-bis(4-hydroxyphenyl)-propane) are reacted using the procedures in Example 1. The resulting product has an N-equivalent weight of 221.

EXAMPLE 3

Formaldehyde, phenol and 1,4-diaminobenzol in mole ratio 2:1:0.5 are reacted using the procedures in Example 1. The resulting product has an N-equivalent weight of 172.

EXAMPLE 4

37.6 kilograms (400 moles) of phenol, 15 kilograms (200 moles) of 40% formaldehyde and 2 kilograms of 10% sulfuric acid are heated to 40° C. in a stirred vessel. The mixture exotherms to 96° C. The mixture is maintained at 96° C. with stirring for 30 minutes. The mixture is cooled to room temperature and allowed to settle. The aqueous layer is removed. The remaining product is a phenol-Novolak mixture with an average number of nuclei of 2, a water content of 15% and a phenol content of 22%. The equivalent weight of phenol is 117.7.

EXAMPLE 5

157.5 grams (2.1 mole) of 40% formaldehyde containing 5 milimoles of potassium hydroxide, 117.7 grams of the product of Example 4 containing 1 mole phenol hydroxyl groups, and 93 grams (1 mole) of aniline are mixed together for 7 minutes at 95° C. with stirring, then heated under reflux conditions for 30 minutes. The mixture is cooled to room temperature, allowed to settle and the aqueous layer is removed. The resulting product is distilled under a vacuum and at a temperature of 123° C. to remove remaining water. The product has an N-equivalent weight of 217.

EXAMPLE 6

A resin containing an average of 1.6 1-oxa-3-aza-tetraline groups per molecule is produced from 1.5 moles of formaldehyde, 1 gram equivalent of the product of Example 4, and 0.8 mole of aniline using the procedures of Example 5. The resulting product has an N-equivalent weight of 240.5.

The following Examples 7-25 are provided to illustrate the preparation of the polymeric resins of the invention. In these examples, some of the epoxide resins identified in Table 1 are used. The remaining epoxide resins in Table 1 are also useful in making the polymeric resins of the invention.

TABLE 1

| Symbol | Epoxide Resin |
|---|---|
| A | 4-(1,2-epoxyethyl)-1,2-epoxycyclohexane |
| B | 1,2,8,9-diepoxy-p-menthane |
| C | 2,2-bis-(3,4-epoxycyclohexyl)-propane |
| D | Bis-(2,3-epoxycyclopentyl)ether (liquid form) |
| E | Bis-(2,3-epoxycyclopentyl)ether (isomer crystalline form) |
| F | 1,2,5,6-diepoxy-4,7-hexahydromethanoindane |
| G | 1,1,1-tris((5-(1,2-epoxy)-4,7-hexahydromethanoindane oxy) methyl)-propane |
| H | 1,2-bis(5(1,2-epoxy)4,7-hexahydromethanoindane oxy)-ethane |
| I | 3,4-epoxycyclohexane carboxylic acid-(3,4-epoxycyclohexylmethyl) ester |
| K | 3,4-epoxy-6-methylcyclohexane carboxylic acid-(3,4-epoxy-6-methylcyclohexylmethyl) ester |
| L | 2-(3,4-epoxy)cyclohexyl-5,5-spiro(3,4-epoxy)-cyclohexane-m-dioxane |
| M | 2-(3,4-epoxy-4-methylcyclohexyl-5,5-spiro(3,4-epoxy)cyclohexane-m-dioxane |
| N | 2-(3,4-epoxy-4-methylcyclohexyl)-5,5-spiro(3,4-epoxy)-4-methyl cyclohexane-m-dioxane |
| O | 2-(3,4-epoxy)cyclohexyl-5,5-spiro(3,4-epoxy)-4-methylcyclohexane-m-dioxane |
| P | 2-(3,4-epoxy)-4,6-dimethylcyclohexyl-5,5-spiro-(3,4-epoxy)-4-methylcyclohexane-m-dioxane |
| Q | 2-(3,4-epoxy)-4,6-dimethylcyclohexyl-5,5-spiro-(3,4-epoxy)-4,6-dimethylcyclohexane-m-dioxane |
| R | Bis-(3,4-epoxy-6-methylcyclohexylmethyl)adipate |
| S | Bis-3,4-epoxycyclohexylmethyl)adipate |
| T | Bis-(3,4-epoxy-cyclohexylmethyl)-terephthalate |
| U | Bis-(3,4-epoxy-6-methylcyclohexylmethyl)-terephthalate |
| V | 4,5-epoxy-hexahydrophthalic acid-bis-(3,4-epoxy-cyclohexylmethyl)ester |

F 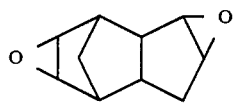

G 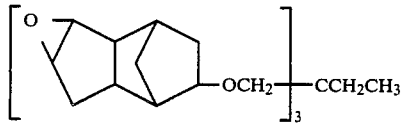

H 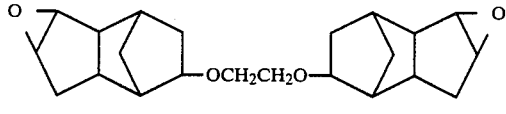

L 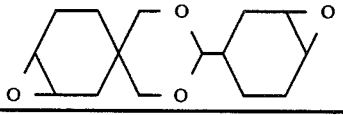

EXAMPLE 7

100 parts of the product of Example 1 are mixed at 140° C. with 100 parts of epoxide resin I and poured under vacuum into a mold for a plate 10 millimeters thick. The mixture is cured for one hour at 180° C., then for one hour at 200° C. and then for two hours at 220° C. Test bodies prepared from the plate show no decomposition at 250° C. These bodies have a bending resistance of 115 MPs, an E modulus of 4800 MPs, an electrical resistance over $10^{15}$ ohms and a loss factor of less than $10^{-2}$. The glass transition temperature is 230° C. The term "glass transition" temperature is used herein to refer to the temperature at which the polymer changes from a brittle, vitreous state to a plastic state.

EXAMPLES 8-23

Cast resin plates were prepared from the resin mixtures given in Table 2 using the method described in Example 7. The epoxide resins used are listed in Table 1. The properties of the cured resins are listed in Table 2.

TABLE 2

| Example No. | 8 | 9 | 10 | 11 | 12 | 13 | 14 | 15 |
|---|---|---|---|---|---|---|---|---|
| 1-Oxa-3-aza-tetraline compound from Example No. | 5 | 5 | 5 | 5 | 5 | 5 | 5 | 5 |
| N-equavalent weight (1) | 217 | 217 | 217 | 217 | 217 | 217 | 217 | 217 |
| Wt. of 1-oxa-3-aza-tetraline compound, g | 100 | 100 | 100 | 100 | 100 | 100 | 100 | 100 |
| Epoxide resin | K | S | L | L | L | L | L | L |
| Epoxide equivalent weight | 140 (3) | 183 (3) | | | 162 (2) | | | |
| Wt. of epoxide, g | 100 | 100 | 100 | 20 | 40 | 66 | 75 | 150 |
| Equivalent ratio (6) | 1.55 | 1.18 | 1.36 | 0.27 | 0.54 | 0.9 | 1.0 | 2.0 |
| Curing cycle | (7) 180° C.→ | | → | → | → | → | → | → |
| | (7) 200° C.→ | | → | → | → | → | → | → |
| | (7) 220° C.→ | | → | → | → | → | → | → |
| Recuring | | | (10) 250° C. | | | | | |
| Behavior at 220° C. | (4) | (4) | (4) | (4) | (4) | (4) | (4) | (4) |
| 250° C. | (4) | (4) | (4) | (4) | (4) | (4) | (4) | (5) |
| Bending resistance at, MPs  25° C. | | 115 | | 100–110 | | | | |
| 220° C. | | | | 65 | | | | |
| 250° C. | | | | 50 | | | | |
| Glass transition temperature, C.° | 220° | 190° | 250° | 280° | 210° | 250° | >260° | >260° | >260° |

| Example No. | 16 | 17 | 18 | 19 | 20 | 21 | 22 | 23 |
|---|---|---|---|---|---|---|---|---|
| 1-Oxa-3-aza-tetraline compound from Example No. | 5 | 5 | 2 | 3 | 6 | 5 | 5 | 5 |
| N-equavalent weight (1) | 217 | 217 | 231 | 172 | 240 | 217 | 217 | 217 |
| Wt. of 1-oxa-3-aza-tetraline compound, g | 100 | 100 | 100 | 100 | 100 | 100 | 100 | 100 |
| Epoxide resin | I | O | R | I | L | R · L | K · A | A |
| Epoxide equivalent weight | 126 (3) | 147 (3) | 197 (3) | 160 (3) | — | — | 70 (3) | |
| Wt. of epoxide, g | 100 | 100 | 100 | 100 | 50 | 50 · 50 | 80 · 20 | 26 |
| Equivalent ratio (6) | 1.7 | 1.5 | 1.2 | 1.36 | 0.75 | — | — | 0.8 |
| Curing cycle | → | → | → | → | → | → | (8) 140° C. | (8) 140° C. |
| | → | → | → | → | → | → | (9) 200° C. | (9) 160° C. |
| | → | → | → | → | → | → | | (9) 200° C. |
| Recuring | | | | | | | | |
| Behavior at 220° C. | (4) | (4) | (4) | (4) | (4) | (4) | (4) | (4) |
| 250° C. | (4) | (4) | (4) | (4) | (4) | (4) | (4) | (5) |
| Bending resistance at, MPs  25° C. | 115 | | | | | | | |
| 220° C. | | | | | | | | |
| 250° C. | | | | | | | | |
| Glass transition temperature, C.° | 230° | 220° | 200° | 240° | 180° | 220° | 220° | 170° |

(1) Calculated from production.
(2) Analytically determined.
(3) Calculated from theoretical formula.
(4) Unchanged
(5) Cracks and bubbles observed.
(6) Ratio of equivalents of 1-oxa-3-aga-tetraline to epoxide.
(7) 1 hour at
(8) 24 hours at
(9) 2 hours at
(10) 3 hours at

EXAMPLE 24

75 grams epoxide resin L are mixed, under vacuum at 120° C. with 100 grams of the 1-oxa-3-aza-tetraline compound according to Example and 200 grams quartz meal, and poured into a mold. The cast piece is cured for 1 hour at 200° C., then for 1 hour at 220° C. The resulting product has a bending resistance of 60 MPs and shows no deformation at 250° C.

EXAMPLE 25

A glass cloth with a glycidyl-propyl silane finish and a surface area of 120 grams per square meter is impregnated with a 60% solution of the resin mixture of Example 21, and dried in a two-step hot air channel at 100°–140° C. Eight layers of the Prepreg are pressed between layers of copper foil for one hour at 180° C. to form a plate. The laminate shows no delamination in the solder bath test at 260° C. The electrical resistance is over $10^{15}$ ohm —cm, the loss factor under 0.01. The bending resistance amounts to 500 MPs.

EXAMPLES 26–28

Examples 26–28 are provided for purposes of comparison. Cast resin plates were prepared from resin mixtures provided in Table 3. In Examples 26 and 27, cycloaliphatic epoxide resins other than the type required by the present invention were used. In Example 28, the monofunctional 1-oxa-3-aza-tetraline compound disclosed in Example 1 of Swiss Pat. No. 579,113 was used. The results of these examples indicate that polymers with less heat stability or lower glass transition temperatures were achieved when compared to the polymeric resins of the invention.

TABLE 3

| Example No. | 26 | 27 | 28 |
|---|---|---|---|
| 1-Oxa-3-aza-tetraline compound from Example No. | 5 | 5 | N—Phenyl-1-oxa-3-ara-tetraline |
| N-equivalent (1) | | | |
| Wt. of 1-oxa-3-aza-tetraline compound, g. | 100 | 100 | 100 |
| Epoxide resin | Tetrahydrophthalic acid diglycidylester | Hexahydrophthalic acid diglycidylester | 1 |
| Epoxide equivalent | | | 140 (1) |
| Wt. of epoxide, g. | 100 | 100 | 40 |
| Equivalent ratio (6) | | | 0.60 |
| Curing cycle | 2 hrs. at 180° C. 1 hr. at 200° C. | 2 hrs. at 180° C. 1 hr. at 200° C. | 2 hrs. at 160° C. 1 hr. at 200° C. |
| Behavior at 220° C. | (5) | (5) | (4) |
| Glass transition temperature, °C. | | | 110° C. |

(1) Calculated from production.
(2) Analytically determined.
(3) Calculated from theoretical formula.
(4) Unchanged
(5) Cracks and bubbles observed.
(6) Ratio of equivalents of 1-oxa-3-aza-tetraline to epoxide.

The polymeric resins of the invention obtained in the above examples show, in comparison with the structurally closest previously known resins, of which the properties are well known, a generally far higher heat resistance, along with very good mechanical properties, especially with high bending and impact resistance. The comparison tests (Examples 26-28) confirm this observation.

While the invention has been explained in relation to its preferred embodiments, it is to be understood that various modifications thereof will become apparent to those skilled in the art upon reading this specification. Therefore, it is to be understood that the invention disclosed herein is intended to cover such modifications as fall within the scope of the appended claims.

I claim:

1. A composition comprising a polymeric resin derived from
   (A) at least one compound containing an average of more than one 1-oxa-3-aza-tetraline group per molecule with
   (B) at least one cycloaliphatic epoxide containing at least two epoxide groups, at least one of said epoxide groups being part of said ring, the mole ratio of (B) to (A) being in the range of about 0.2 to about 2.

2. The composition of claim 1 wherein component (B) has at least one epoxide group directly attached to said ring.

3. The composition according to claim 1, wherein said 1-oxa-3-aza-tetraline groups include an aromatic substituent at the nitrogen atom.

4. The composition of claim 1 wherein component (A) is the reaction product of at least one amine, at least one phenol, and formaldehyde.

5. The composition of claim 4 wherein said phenol is selected from the group consisting of phenol, m- and p-cresol, m- and p-ethyl-phenol, m- and p-isopropyl-phenol, m- and p-methoxy-phenol, m- and p-ethoxy-phenol, m- and p-isopropyloxy-phenol, m- and p-chlorophenol and B-naphthol.

6. The composition of claim 4 wherein said phenol is selected from the group consisting of 4,4'-dihydroxy-diphenylmethane, 3,3'-dihydroxy-diphenylmethane, 2,2-bis-(4-hydroxy-phenyl)-propane, 4,4'-dihydroxystilbene, hydroquinone, pyrocatechin and resorcin.

7. The composition of claim 4 wherein said amine is selected from the group consisting of aniline, o-, m- and p-phenylene diamine, benzidine, 4,4'-diaminodiphenyl methane, and 2,2-bis-(aminophenyl)propane.

8. The composition of claim 1 wherein component (A) is a Novolak resin.

9. The composition of claim 1 wherein component (B) has an equivalent weight in the range of about 70 to about 250.

10. The composition of claim 1 wherein component (B) has an equivalent weight in the range of about 120 to about 200.

11. The composition of claim 1 wherein component (B) is selected from the group consisting of 2-(3,4-epoxy)cyclohexyl-5,5-spiro(3,4-epoxy)cyclohexane-m-dioxane, 1 to 4 times methylated 2-(3,4-epoxy)cyclohexyl-5,5-spiro(3,4-epoxy)cyclohexane-m-dioxane, 4-(1,2-epoxyethyl)-1,2-epoxycyclohexane, 1,2,8,9-diepoxy-p-methane, 2,2-bis(3,4-epoxycyclohexyl)propane, bis-(2,3-epoxycyclopentyl)ether, 1,2,5,6-diepoxy-4,7-hexahydromethanoindane, bis-(3,4-epoxy-cyclohexylmethyl)adipate, bis(3,4-epoxy-6-methylcyclohexylmethyl)adipate, bis(3,4-epoxy-cyclohexylmethyl)terephthalate, bis(3,4-epoxy-6-methyl-cyclohexylmethyl)-terephthalate,3,4-epoxy-cyclohexane carboxylic acid-(3,4-epoxy-cyclohexylmethyl)ester, 3,4-epoxy-6-methylcyclohexanecarboxylic acid-(3,4-epoxy-6-methylcyclohexylmethyl)ester, 1,2-bis-(5(1,2-epoxy)-4,7-hexahydromethanoindaneoxy)-ethane, 1,1,1-tris((5-(1,2-epoxy)-4,7-hexahydromethynoindaneoxy)-methyl)-propane and 4,5-epoxyhexahydrophthalic acid-bis-(3,4-epoxy-cyclohexylmethyl)ester.

12. The composition of claim 1 wherein component (B) is selected from the group consisting of 2-(3,4-epoxy)cyclohexyl-5,5-spiro(3,4-epoxy)cyclohexane-m-dioxane, 1 to 4 times methylated 2-(3,4-epoxy)cyclohexyl-5,5-spiro(3,4-epoxy)cyclohexane-m-dioxane, bis(3,4-epoxy-cyclohexylmethyl)adipate, bis(3,4-epoxy-6-methylcyclohexylmethyl)adipate, 3,4-epoxy-cyclohexane-carboxylic acid-(3,4-epoxy-cyclohexylmethyl)ester and 3,4-epoxy-6-methylcyclohexane carboxylic acid-(3,4-epoxy-6-methylcyclohexylmethyl)ester.

13. The composition of claim 1 wherein component (B) is represented by the formula $$X—Y$$

wherein:
X is a 3,4-epoxycyclohexyl group or a mono- or dimethyl substituted 3,4-epoxycyclohexyl group; and
Y is a group represented by the formula

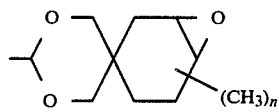

wherein n is a number in the range of from zero to 2, or a group represented by the formula

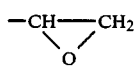

or a group represented by the formulae

or

—CH$_2$—Z—CH$_2$—X wherein:
X is as defined above, and Z is derived from an aliphatic, cycloaliphatic or aromatic dicarboxylic acid group.

14. The composition of claim 1 wherein the mole ratio of (B) to (A) is in the range of from about 0.8 to about 1.5.

15. The composition of claim 1 wherein components (A) and (B) are reacted at a temperature in the range of about 50° C. to about 300° C.

16. The composition of claim 1 wherein components (A) and (B) are reacted at a temperature in the range of about 100° C. to about 250° C.

17. The composition of claim 1 wherein components (A) and (B) are reacted at a temperature in the range of about 140° C. to about 230° C.

18. The composition of claim 1 wherein components (A) and (B) are reacted in the presence of an effective amount of catalyst to accelerate the reaction.

* * * * *